United States Patent
Barrett

(10) Patent No.: US 7,727,179 B2
(45) Date of Patent: Jun. 1, 2010

(54) FLOW ADAPTIVE ASPIRATION TUBING AND DEVICES

(76) Inventor: Graham D. Barrett, 56 Dampier Avenue, City Beach (AU) 6015

( * ) Notice: Subject to any disclaimer, the term of this patent is extended or adjusted under 35 U.S.C. 154(b) by 425 days.

(21) Appl. No.: 10/456,287

(22) Filed: Jun. 6, 2003

(65) Prior Publication Data

US 2004/0039351 A1 Feb. 26, 2004

(30) Foreign Application Priority Data

Jun. 7, 2002 (AU) .................................. PS2801

(51) Int. Cl.
*A61M 1/00* (2006.01)
(52) U.S. Cl. ........................................................ 604/27
(58) Field of Classification Search ................ 604/246, 604/272, 523, 317, 323, 326, 34, 118–119, 604/313, 540, 542, 19, 27; 433/96; 138/128
See application file for complete search history.

(56) References Cited

U.S. PATENT DOCUMENTS

| 1,596,754 | A | * | 8/1926 | Moschelle | 604/541 |
| 3,604,420 | A | * | 9/1971 | Vaillancourt | 604/129 |
| 5,741,226 | A | * | 4/1998 | Strukel et al. | 604/35 |

FOREIGN PATENT DOCUMENTS

| DE | 19651676 | 6/1997 |
| DE | 19628252 | 1/1998 |
| FR | 2740028 | 4/1997 |

* cited by examiner

*Primary Examiner*—Nicholas D Lucchesi
*Assistant Examiner*—Theodore J Stigell
(74) *Attorney, Agent, or Firm*—Pearne & Gordon LLP

(57) ABSTRACT

Aspiration tubing for use in a phacoemulsification system is provided having a modified lumen that enhances resistance of fluid flow through the lumen to reduce post-occlusion surge, the modification comprising recesses or protuberances formed in the interior surface of the lumen, a freely-moving object disposed in the flow path of the lumen, or one or more bends.

1 Claim, 4 Drawing Sheets

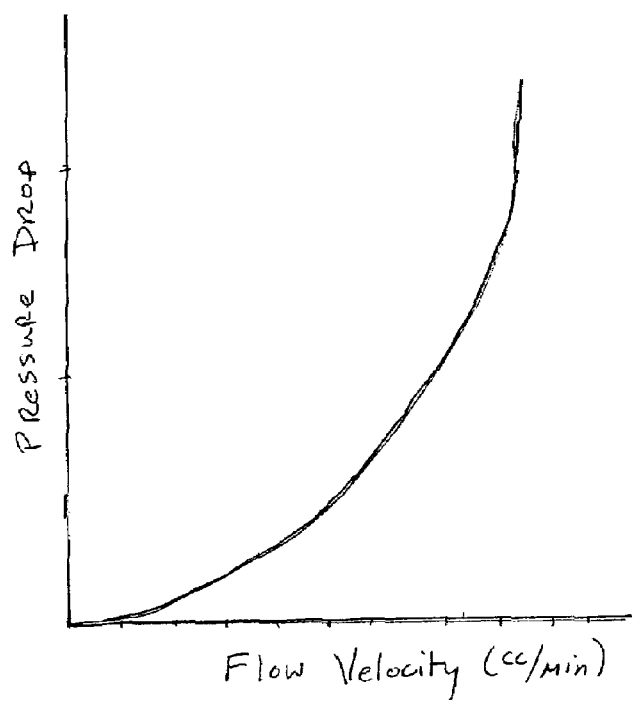
FIG. 9
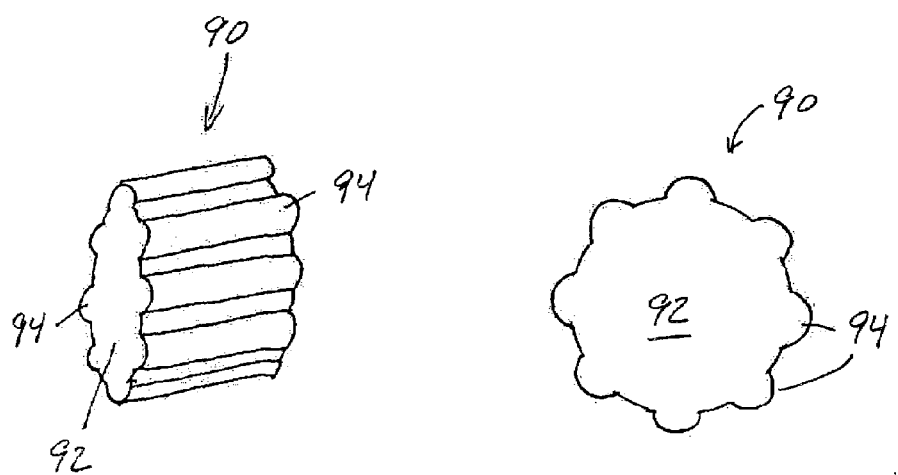
FIG. 10A
FIG. 10B

FLOW ADAPTIVE ASPIRATION TUBING AND DEVICES

FIELD OF THE INVENTION

The present invention relates generally to apparatus for performing phacoemulsification, in particular to flow adaptive aspiration tubing for use in conjunction with phacoemulsification systems.

BACKGROUND OF THE INVENTION

The crystalline lens of the human eye transmits and focuses light and is located behind the iris attached to the wall of the eye by suspensory ligaments known as the zonules. The lens consists of a more rigid central nucleus surrounded by peripheral cortical material, which has a softer consistency. A fine membrane known as the capsule contains the entire lens.

Cataract formation refers to a loss of transparency of the crystalline lens of the eye and is a common occurrence with age. This results in a progressive reduction in vision, which can be restored with surgery. Cataract surgery involves removal of the cataractous lens and insertion of a plastic intraocular lens to replace the crystalline lens. Removal of the cataractous lens is accomplished using ultrasonic energy to fragment and aspirate the lens by a technique known as phacoemulsification.

During such surgery, a central opening is formed in the anterior portion of the capsule to permit access to the lenticular material. An ultrasonic handpiece, typically including a needle having an outer wall and central lumen, is then inserted, contacted against and caused to fragment the lens. An elastomeric sleeve surrounding the needle provides a conduit irrigating the eye to replace material aspirated through the needle. Once the nuclear material of the lens has been removed with the assistance of ultrasonic energy, softer cortical material may be aspirated with an irrigation/aspiration cannula.

In both phases of the procedure it is important that the anterior chamber is maintained at a positive pressure and constant volume to prevent collapse, so as to prevent trauma to sensitive ocular tissues. Contact with the endothelial cells lining the posterior surface of the cornea or the iris can result in irreparable damage. Even more common is inadvertent contact or aspiration of the posterior capsule, which prevents the escape of the fluid contained in the posterior chamber of the eye known as the vitreous humour. Such inadvertent contact may result in rupture of the posterior capsule membrane.

Rupture of the posterior capsule and loss of the vitreous humour increases the risk of retinal detachment and cystoid macular oedema after cataract surgery, with subsequent loss of vision. Furthermore if the posterior capsule is disrupted during surgery it may not be feasible to properly place an intraocular lens in in the capsular bag remnant of the original lens, again resulting in a less favorable outcome than might be anticipated in uncomplicated surgery.

Maintaining a stable pressure and volume in the anterior chamber when performing phacoemulsification is of paramount concern. Optimal fluid dynamics implies sustaining a stable pressure and volume in the anterior chamber when performing phacoemulsification. Aspiration of fluid from the anterior chamber must be balanced by adequate infusion. The desired state of fluid balance may be summarized in the equation: $F_i = F_o$ — Inflow ($F_i$) should equal Outflow ($F_o$). To avoid chamber collapse the pressure in anterior chamber ($P_{ac}$) also must be greater than atmospheric pressure ($P_a$) and greater than vitreous pressure ($P_v$)–$P_{ac}$>$P_a$>$P_v$.

The pressure in the anterior chamber depends on the infusion pressure, which is the difference between the irrigation pressure head ($P_i$), related to the irrigation bottle height, and the drop in pressure due to resistance to the inflow of irrigation fluid ($P_d$)–$P_a$=$P_i$–$P_d$. The anterior chamber pressure preferably should be maintained at a constant level to avoid alterations in chamber volume, which manifest as an unstable chamber during surgery.

A conventional apparatus used in cataract surgery includes a console containing a pump system used to generate vacuum and flow as well as the electrical circuitry that provides energy and control for the phacoemulsification handpiece. The pump systems are connected to the phacoemulsification handpiece and irrigation and aspiration cannula by tubing so that fluid and lens material can be aspirated from the eye.

Several types of pump systems are known for providing aspiration of fluid and lens material during phacoemulsification and cortical aspiration. The first type are positive fluid displacement pumps, such as a peristaltic pump. In such systems, fluid flow is generated by drawing suction through the tubing and significant vacuum may be achieved if the tubing becomes occluded. In other pump systems, such as a venturi pump, suction is generated in a cassette and the subsequent flow and aspiration of fluid from the eye is related to that preset suction level.

For either pump system, the sequence of removal of nuclear and cortical material is similar. Fluid is aspirated from the anterior chamber via suction applied through the phacoemulsification needle or irrigation/aspiration cannula and the associated aspiration tubing. This suction attracts nuclear or cortical material to the needle or cannula and may result in larger fragments occluding the tip or aspiration port.

The suction level within the tubing then rises until the negative pressure generated overcomes the resistance of the lenticular material, which is then aspirated down the tubing. This in turn causes a rapid equalization of pressure between the anterior chamber and the rest of the system, with a concomitant rapid increase in flow and drop in chamber pressure. This phenomenon is typically referred to as "post occlusion surge" and may cause a forward movement of the posterior capsule as the chamber pressure and volume fluctuates.

Vacuum applied by the phacoemulsification handpiece may be modulated by foot pedal control, thereby causing the pump system to respond by venting or equalizing the pressure in the system either to fluid or to air. The venting, however, occurs, some distance from the handpiece and anterior chamber and there is typically a lag before the vacuum in the tubing is restored to a positive pressure and the pressure in the anterior chamber is restored to the normal resting or unoccluded level.

Accordingly, it would be desirable to reduce the surge in flow rate that occurs with rapid fluctuations in vacuum pressure associated with occlusion of the phacoemulsification needle. Such control advantageously could reduce fluctuations in chamber pressure and shorten the time to attain equilibrium pressure, thereby enhancing safety of the surgical procedure and reducing the risk of inadvertent rupture of the posterior capsule.

One potential method for reducing fluid surges in the aspiration tubing is to reduce the maximum vacuum levels that are generated by the pump system. High vacuum levels, however, are advantageous in capturing fragments of nuclear material so that the fragments may be fractured into smaller pieces. It is therefore desirable to maintain high vacuum levels while reducing the high flow rates associated with surges that occur at those high levels of vacuum.

Another approach is to increase the resistance in the aspiration tubing by reducing the lumen or increasing the length of the aspiration tubing. While reducing the lumen size may be effective, the internal diameter of typical phacoemulsification tubing is generally about 1.5 mm, and any further reduction in diameter is likely to result in obstruction of the aspiration tubing by lens material. Increasing the tubing length may be accomplished by coiling the tubing to add further hydrodynamic resistance. In both cases, however, the increased resistance of the tubing exists for all vacuum levels. This is undesirable, as it would be preferable to maintain undiminished aspirational flow rates at low vacuum levels to facilitate attraction of lens fragments prior to occlusion.

In view of the foregoing, it would be desirable to provide a phacoemulsification system including flow adaptive aspiration tubing that automatically increases flow resistance in response to higher flow rates.

It further would be desirable to provide a phacoemulsification system including flow adaptive aspiration tubing that induces turbulent flow at lower flow velocities.

It would be yet further desirable to provide a phacoemulsification system including flow adaptive aspiration tubing that provides improved anterior chamber stability at higher vacuum levels.

SUMMARY OF THE INVENTION

In view of the foregoing, it is an object of the present invention to provide a phacoemulsification system including flow adaptive aspiration tubing that automatically increases flow resistance in response to higher flow rates.

It is another object of the present invention to provide a phacoemulsification system including flow adaptive aspiration tubing that induces turbulent flow at lower flow velocities.

It is a further object of this invention to provide a phacoemulsification system including flow adaptive aspiration tubing having a modified lumen that defines longitudinal flutes arranged in a spiral pattern.

It is another object of the present invention to provide a phacoemulsification system including flow adaptive aspiration tubing that provides improved anterior chamber stability at higher vacuum levels.

These and other objects of the present invention are accomplished by providing flow adaptive tubing for use with phacoemulsification systems, wherein the tubing has a lumen surface that enhances turbulent flow through the tubing at relatively low flow velocities.

In one preferred embodiment the aspiration tubing constructed in accordance with the principles of the present invention comprises topographical features, such as spiral flutes, inwardly projecting protuberances, ridges or recesses, formed on an inner surface of the aspiration tubing. The features may be provided along the entire length of the tubing or only along discrete portions of the length, and may extend around the entire circumference of the lumen or only parts thereof.

In an alternative embodiment the aspiration tubing comprises a freely-moving object, such as a vane or a propeller, disposed within the lumen of the tubing. In a yet further alternative embodiment, the aspiration tubing comprises one or more bends along the length of the tubing that are configured to enhance hydrodynamic resistance at higher flow velocities.

BRIEF DESCRIPTION OF THE DRAWINGS

The above and other objects and advantages of the present invention will be apparent upon consideration of the following detailed description, taken in conjunction with the accompanying drawings, in which like referenced characters refer to like parts throughout, and in which:

FIG. 9 is a chart showing the velocity of fluid flow within the aspiration tubing plotted against the drop in pressure due to frictional forces within the aspiration tubing; and FIGS. 10A and 10B are perspective and plan views, respectively, of an extrusion die used to extrude the aspiration tubing shown in FIG. 2.

DETAILED DESCRIPTION OF THE INVENTION

Overview of a Preferred Phacoemulsification System

Figure 1:
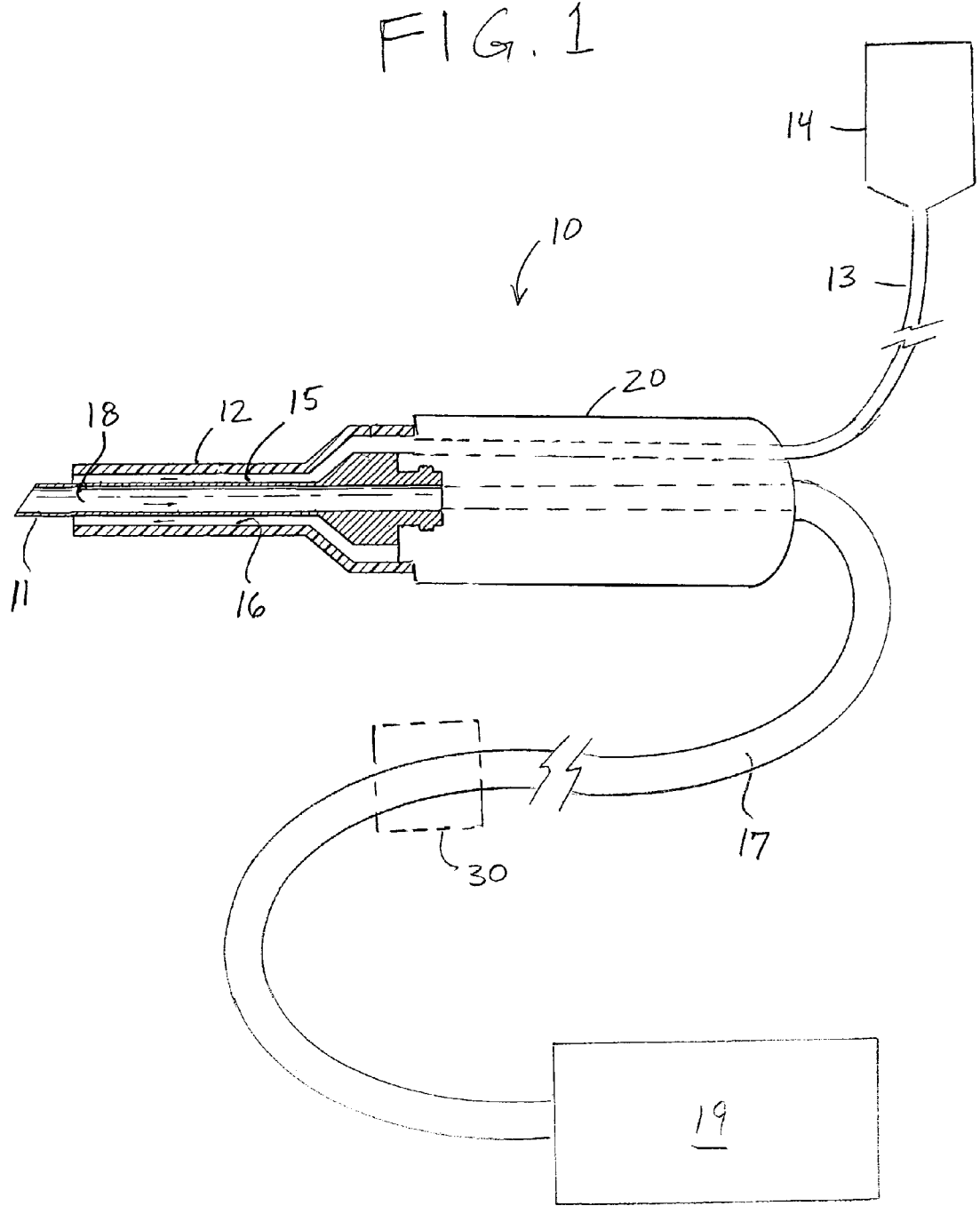
FIG. 1 is a side-sectional view of a phacoemulsification system suitable for use with the flow adaptive aspiration tubing of the present invention.

Referring to FIG. 1, a phacoemulsification system suitable for use with the flow adaptive tubing of the present invention is described. Phacoemulsification system 10 comprises phacoemulsification needle 11 coupled to ultrasonic handpiece 20 and surrounded by elastomeric sleeve 12. Handpiece 20 is typically coupled to a controller (not shown), that causes needle 11 to vibrate at ultrasonic frequencies. When needle is contacted against a cataractous lens, vibration of needle 11 causes the needle to fragment the nuclear material of the lens.

Irrigation line 13 is coupled in fluid communication between a source of irrigation fluid 14 and handpiece 20 so that irrigation fluid is delivered into the eye via annulus 15 formed between needle 11 and interior surface 16 of elastomeric sleeve 12. Aspiration tubing 17 is coupled in fluid communication between lumen 18 of needle 11 and vacuum source 19, to permit the aspiration of fragmented nuclear material from a patient's eye.

In operation, ultrasound energy is applied to the nuclear material of the patient's lens by phacoemulsification needle 11. During the phacoemulsification process, irrigation fluid is supplied to the eye from irrigation reservoir 14 via annulus 15 between needle 11 and elastomeric sleeve 12. Simultaneously, fragmented nuclear material is withdrawn through needle lumen 18 and aspiration tubing 17. As described hereinabove, larger fragments that are caused to engage needle 11 by virtue of suction drawn through lumen 18 may cause surges in flow rates of material aspirated through lumen 18 and wide fluctuations of the pressure within the eye. The aspiration tubing of the present invention is expected to moderate such post-occlustion surges and reduce the resulting pressure fluctuations.

Description of the Flow Adaptive Aspiration Tubing of the Present Invention

In accordance with the principles of the present invention, phacoemulsification system 10 of FIG. 1 is provided with aspiration tubing having a lumen modified to enhance hydrodynamic resistance to fluid flow at higher flow rates. The modification may take one of a number of forms, and comprise topographic features along the interior surface of the tubing, freely-movable obstructions within the flow path, or one or more flow-redirecting bends.

Figure 2:
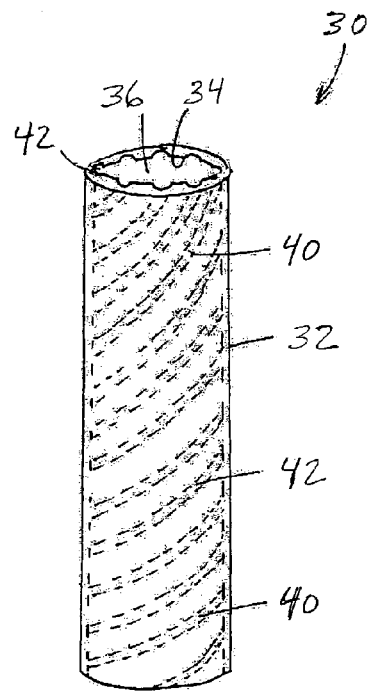
FIG. 2 is a perspective view of a length of aspiration tubing in accordance with a preferred embodiment of the present invention.

Referring now to FIG. 2, a first illustrative embodiment of adaptive aspiration tubing 30 of the present invention is described. Tubing 30 has outer surface 32 and inner surface 34 that defines lumen 36. In accordance with the principles of the present invention, inner surface 34 comprises topographical features 40 that enhance flow resistance at higher flow rates by enhancing turbulent flow within the lumen. Features 40 may be provided along the entire length of the tubing or only along one or more discrete segments of the tubing. In addition, the features may extend entirely around the circumference of tubing 30 as shown in FIG. 2, or may extend for only limited arcs of the circumference.

In one preferred embodiment, features 40 comprise spiral flutes or recesses 42 formed as grooves in the inner surface of the tubing. Recesses 42 illustratively are disposed at regular intervals along the length of the tubing and around the circumferential periphery of the inner surface. Recesses 42 may have a semi-annular cross-section (as shown in FIG. 2) or alternatively may include a cross-sectional profile of a semi-ellipse, rectangular, triangular, square, diamond or other suitable shape.

Still referring to FIG. 2, recesses 42 produce turbulent flow within lumen 36 without increasing the likelihood that a large fragment will obstruct the lumen. In particular, recesses 40 enhanced turbulence by increasing the hydrodynamic resistance of fluid passing through the tubing. Advantageously, because flow resistance increases at higher flow rates, risks associated with fluid surge and accompanying pressure fluctuations that could cause collapse or partial collapse of the anterior chamber of the eye are reduced. In addition, features 40 alter the flow pattern within the lumen such that the flow becomes turbulent at lower flow velocities.

Figure 3:
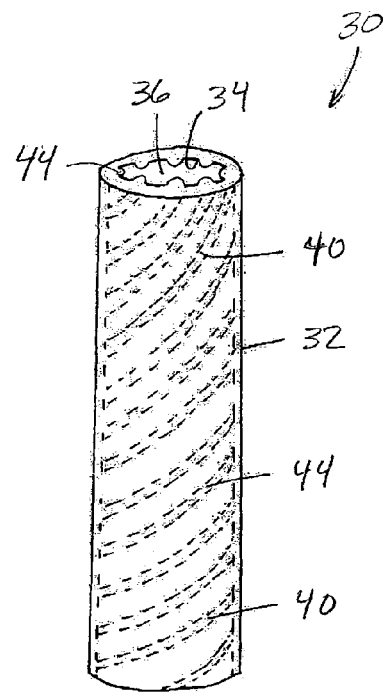
FIG. 3 is a perspective view of a length of aspiration tubing in accordance with another embodiment of the present invention.

Referring now to FIG. 3, alternative embodiments are described, wherein the topographical features 40 comprise raised protuberances 44, such as ridges or lugs, that project from the inner surface of tubing into lumen 36. Protuberances 44 may be arranged as a series of semi-cylindrical ridges disposed in a spiral pattern at regular intervals along the length of the tubing and around the circumferential periphery of lumen 36. Alternatively, protuberances 44 may extend only partially around the circumference of lumen 36, or only along selected portions of the tubing length. Like recesses 42, protuberances 44 enhance hydrodynamic resistance within tubing 30 and induce turbulent flow at lower flow velocities and vacuum levels than otherwise encountered in previously known aspiration tubing.

Figure 4:
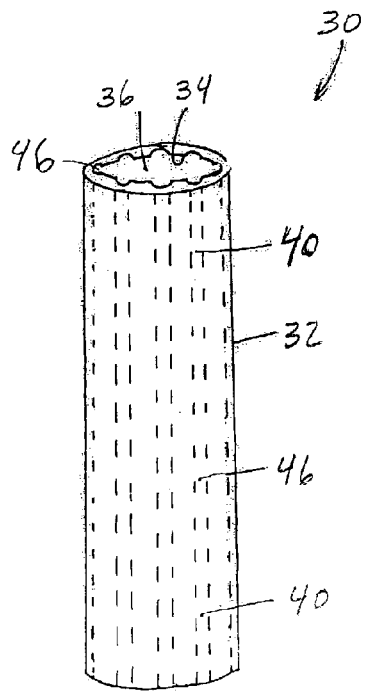
FIG. 4 is a perspective view of a length of aspiration tubing in accordance with an additional embodiment of the present invention.
Figure 5:
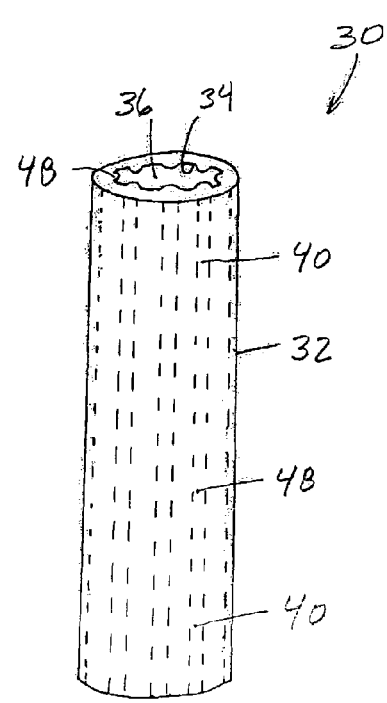
FIG. 5 is a perspective view of a length of aspiration tubing in accordance with a further embodiment of the present invention.

In FIGS. 4 and 5, further alternative embodiments are depicted, in which topographical features 40 comprise longitudinal recesses 46 (FIG. 4) or longitudinal protuberances 48 (FIG. 5) formed in the inner surface of tubing 30. Longitudinal recesses 46 or protuberances 48 are shown disposed substantially parallel to each other and spaced at regular intervals around the circumferential periphery of lumen 36. Alternatively, recesses 46 or protuberances 48 may extend only partially around the circumference of lumen 36, or only along selected portions of the tubing length.

As further would be understood by those of skill in the art, any combination of two or more of the above described topographical features may be provided on the inner surface of the aspiration tubing without departing from the scope of the present invention.

Figure 6:
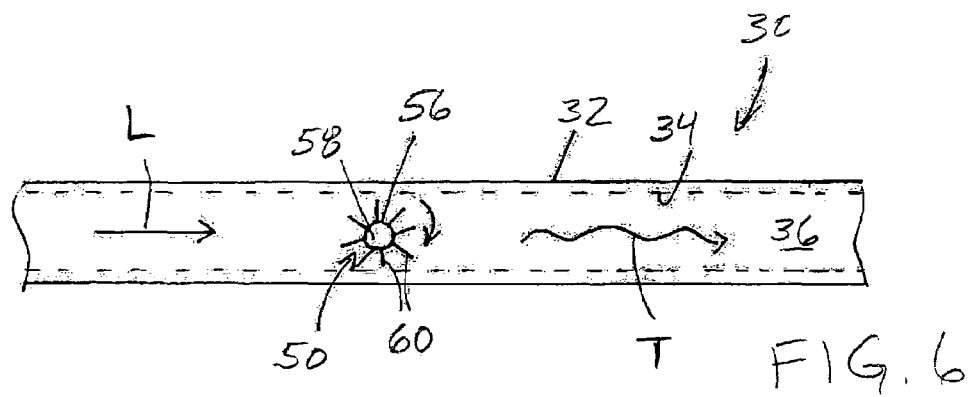
FIG. 6 is a side-sectional view of a length of aspiration tubing in accordance with another embodiment of the present invention including a rotating vane disposed within the aspiration tubing.
Figure 7:
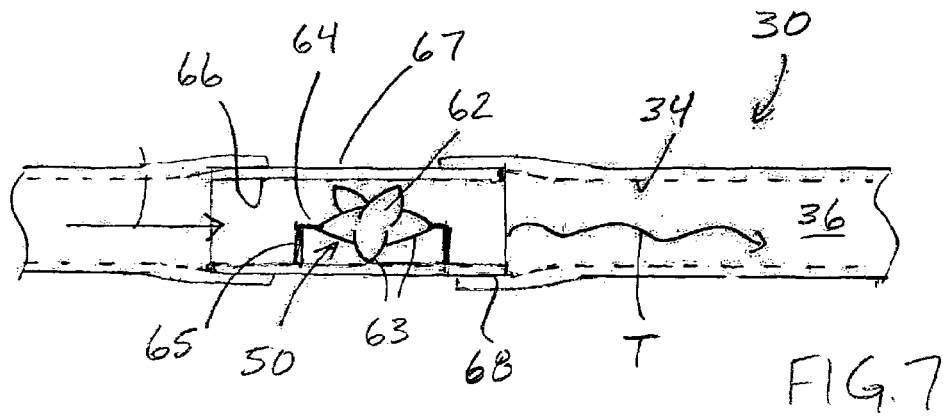
FIG. 7 is a side-sectional view of a length of aspiration tubing in accordance with an additional embodiment of the present invention including a rotating propeller disposed within the aspiration tubing.

Referring now to FIGS. 6 and 7, and in accordance with another aspect of the present invention, aspiration tubing 30 comprises a freely-moving object 50, illustratively, a vane or propeller, disposed within lumen 36. Object 50 is configured to fit within tubing 30 so that it disrupts laminar flow of fluid within lumen 36 and induces turbulence. In FIGS. 6 and 7, laminar flow is indicated by straight arrow L and turbulent flow is indicated by curved arrow T. The induced turbulence increases hydrodynamic resistance within lumen 36, and is a function of the flow velocity within the tubing.

By way of example, freely-moving object 50 may comprise vane 56 (FIG. 6) mounted within lumen 36 on hub 58 and having a plurality of arms 60. Alternatively, as depicted in FIG. 7, freely-moving object 50 may comprise propeller 62 having a plurality of projections 63. Propeller 62 is mounted on axle 64 supported on arms 65 within lumen 66 of separate short longitudinal segment 67. Segment 67 includes adapters 68 at either end so that freely-moving object 50 may be used in conjunction with previously-known aspiration tubing. Of course, as will be appreciated by those of skill in the art, freely-moving object 50 may take on other shapes without departing from the scope of the present invention. In addition, flow through the aspiration tubing may be modified using more than one freely-moving object to disrupt laminar flow.

Figure 8:
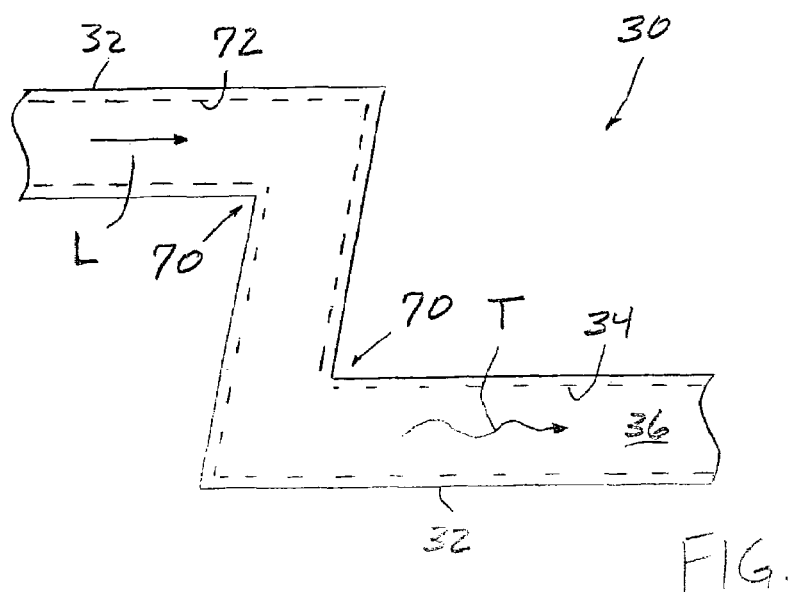
FIG. 8 is a side-sectional view of a length of aspiration tubing including a pair of bends in accordance with a further embodiment of the present invention.

Referring to FIG. 8, another alternative embodiment of aspiration tubing of the present invention is described, in which aspiration tubing 30 comprises one or more angular bends 70. Bends 70 cause abrupt changes in the direction of fluid flowing within lumen 72, so that an initially laminar flow (as indicated by straight arrow L) becomes turbulent flow (as indicated by curved arrow T) after the fluid passes through the one or more angular bends. Preferably, the bend angles are less than or equal to 90°. As for the embodiment of FIG. 7, the embodiment of FIG. 8 may be implemented as a separate segment of rigid tubing that includes one or more bends, and adapters for coupling the segment in-line with previously-known aspiration tubing.

As noted above, previously-known aspiration tubing used in cataract surgery has a smooth inner surface. The rate of fluid flow within such tubing is typically laminar and may be described by the Hagen-Poiseuille equation:

$$Q = P \times \pi \times D^4 / (8 \times l \times v)$$

where Q is the volume flow rate,

P is the pressure differential,

D is the cross sectional diameter of the tubing, l is the length of the restricting diameter, and v is the viscosity of the fluid.

The point at which the flow of fluid within the tubing becomes turbulent is determined by the Reynolds number:

$$Re = d \times V \times D/v$$

where Re is Reynolds number,
V is the fluid velocity,
D is the cross sectional diameter of the tubing and
v is the fluid viscosity.

Experiments show that flow is likely to be laminar if Reynolds number is less than 2000 (the lower critical Reynolds number) and turbulent if it exceeds 4000 (the upper critical Reynolds number). The nature of flow in tubing is uncertain when the Reynolds number is between 2000 and 4000.

Increasing the roughness of the inner wall surface of the tubing increases resistance to flow and tends to induce turbulent flow. When fluid flows through a length of modified tubing that lacks a circular cross section (e.g., FIGS. 2-5), the Reynolds number may be calculated using the equivalent diameter de where:

$$de = 4 \times A/P,$$

where A is the cross section of flow area and
P is the cross-sectional wetted perimeter. Altering the profile of tubing therefore promotes turbulent flow.

When fluid flow is laminar most of the shearing action and friction between layers of fluid takes place away from the wall. The wall surface has relatively little effect on the friction factor (f) which varies inversely with the Reynolds number according to f=64/Re, where Re is the Reynolds number. By contrast, when flow is turbulent the nature of the inner surface of the tubing has a significant effect on the friction factor, because much of the shearing action and resulting friction takes place near the topographical features. The Relative roughness may be defined as:

$$\epsilon_R = \epsilon/d$$

where $\epsilon$ is the height of the surface roughness and d is the tube diameter.

The Moody diagram and foregoing formula may be used to calculate the friction factor (f) for fluid flow in tubing:
$f=0.0055*(1+(20000 \times \epsilon_R + 10^6/Re)^{1/3})$.

Accordingly, modifying the inner surface of the tubing to produce an uneven surface causes flow within the tubing to become turbulent at lower velocities and vacuum levels and thus increases the resistance to flow. Turbulent flow can be described by the Bernoulli equation:

$$Q = SQRT(P \times \pi^2 \times D^4)/(8 \times d))$$

where Q is the volume flow rate,
P is the pressure differential,
D is the cross sectional diameter of the tubing,
l is the length of the restricting diameter,
v is the viscosity of the fluid and
d is the density of the fluid.

For the same pressure differential that is determined by the vacuum level generated by the vacuum, the flow rate will be less due to the increased resistance produced by turbulent flow for the same diameter and length of tubing.

Furthermore, the resistance afforded to fluid flow by the modified aspiration tubing will be relatively unchanged at low vacuum levels but increases proportionally as the vacuum levels rise due to the transition from laminar to turbulent flow (which occurs at lower vacuum level than in previously-known tubing with a smooth internal surface). The drop in pressure due to flow resistance varies as the square of the velocity. Therefore, as depicted in FIG. 9, the drop in pressure plotted against the velocity of fluid flow forms a parabola, wherein a relatively small change in fluid velocity results from a relatively large percentage drop in pressure compared to tubing with a lower frictional resistance and laminar flow.

Advantageously, the provision of topographical features on the inner surface of the tubing does not reduce the efficiency of the phacoemulsification needle in attracting fragments of nuclear material. When occlusion of the needle tip occurs, the initial rise in vacuum within the tubing is similar to previously-known tubing, but the rise time slows as the vacuum level is increased. When the occlusion resistance is overcome, the immediate flow of fluid due to the negative pressure in the aspiration line will be less than with previously-known tubing. Advantageously, this reduces both the magnitude and duration of post-occlusion surge.

The present invention provides modified aspiration tubing with increased flow resistance at higher vacuum levels. This provides a more stable anterior chamber pressure and volume than that encountered with previously-known aspiration tubing. In addition, the aspiration tubing of the present invention enables higher vacuum levels to be employed during phacoemulsification. Higher vacuum levels increase the attraction of nuclear fragments to the needle tip and facilitate the fracture of the fragments into smaller pieces by a second instrument. Moreover, because the cross sectional area and the length of the modified aspiration tubing can be formed to be the same as with previously-known aspiration tubing, the likelihood of obstruction by fragments of lens material is not increased.

Previously-known aspiration tubing may be formed from extruded plastic materials, wherein the unpolymerized plastic flows out through a conical extrusion nozzle provided with a central die. The shape of the die determines the cross-sectional profile of the internal lumen of the aspiration tubing and is usually cylindrical in form. The speed of extrusion and relationship between the central die and surrounding nozzle determines the wall thickness.

Referring to FIGS. 10A and 10B, a die suitable for producing aspiration tubing with a fluted spiral inner lumen (as shown in FIG. 2) is described. Die 90 resembles a gear and has central cylindrical portion 92 and a plurality of semi-circular protuberances 94 spaced at substantially equal intervals around its outer periphery. By rotating the extruded plastic material as it exits the extrusion nozzle, a spiral pattern of grooves or flutes is formed in the internal surface of the lumen. The speed of rotation determines the pitch of the spiral pattern. Suitable materials for manufacturing the aspiration tubing of the present invention include polyvinyl chloride and silicones. As would be understood by those of skill in the art, the modified aspiration tubing can be fabricated by other methods than the above-described extruded molding method without departing from the scope of the present invention.

Central cylindrical portion 92 and protuberances 94 preferably are dimensioned so that the cross sectional surface area of the lumen of the fluted spiral tubing is equivalent to that of previously-known tubing having a circular cross section. Further, the arc length of each semi-circle protuberance along the circumference of central cylindrical portion 92 may be calculated as follows:

$$C = 2 \times \pi \times R/12$$

where R=radius of central cylindrical core.

The central angle $\alpha$ subtended by each semi-circle in radians is given by:

$$\alpha = C/R$$

where C=chord length d of each semi-circle:

$$d=2\times R\times \sin(\alpha/2)$$

The sagittal height h of the flute is given by:

$$h=R-\sqrt{(R^2-r^2)}$$

where r=radius of flute semi-circle

The area S of the segment of produced by intersection of semi-circular protuberance of the flute with the circumference of central cylindrical portion 92 is:

$$S=r^2\times A\ \text{COS}((r-h)/r)-\sqrt{(2\times r\times h-h^2)}\times(r-h)$$

The area f of the flute is given by:

$$f=(r^2\times\pi)/2-S$$

The total area T of fluted tube is given by:

$$T=R^2\times\pi-8\times f$$

According to one preferred embodiment, the modified spiral fluted aspiration tubing of the present invention has an internal diameter of about 1.5 mm and an external diameter of about 3.12 mm. It should be noted that tubing with a lumen having an internal diameter of 1.34 mm and 8 equally-spaced flutes with a radius of 0.173 mm will have the same total cross sectional area as previously-known tubing with a lumen having an internal diameter of 1.5 mm. The modified aspiration tubing of the present invention may be constructed with similar connectors attached to the proximal and distal ends as previously-known tubing, and thus have the same overall length.

Although the invention is described with reference to ultrasound as an energy source to remove the cataract, the modified aspiration tubing also may be used with any method of cataract removal where other energy sources such as laser, sonic, rotary tips, impellers, hydro jet and mechanical methods are used to fragment the cataract and the lens material is removed by aspiration. In addition, it is envisioned that the modified aspiration tubing may be advantageously employed in other medical applications wherein fluids or tissues are aspirated.

Further, as noted hereinabove, the entire length of aspiration tubing may include the modified lumen. Alternatively, as further noted above, the modified aspiration tubing may be formed as either a flexible or rigid segment that may be inserted into a previously-known aspiration line as a separate device. Further, a three-way tap may be provided within the aspiration line to permit bypass or inclusion of the modified aspiration tubing in the aspiration circuit, and thereby alter the rate of fluid flow within an internal lumen of the aspiration line.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A phacoemulsification system comprising:
a phacoemulsification needle;
an ultrasonic handpiece arranged to vibrate at ultrasonic frequencies, the ultrasonic handpiece being coupled to the phacoemulsification needle;
a sleeve surrounding the phacoemulsification needle, wherein an annulus is defined between the sleeve and the phacoemulsification needle;
a source of irrigation fluid;
an irrigation line coupled in fluid communication between the source of irrigation fluid and the handpiece so that irrigation fluid is delivered through the annulus between the sleeve and the phacoemulsification needle,
a vacuum source;
a length of aspiration tubing extending between the ultrasonic handpiece and the vacuum source and being coupled in fluid communication between the phacoemulsification needle and the vacuum source;
the aspiration tubing forming a lumen having an interior surface and first and second ends;
wherein the interior surface of the lumen of the aspiration tubing extends between the first and second ends thereof and the aspiration tubing includes a means for enhancing the turbulence of fluid flow within the lumen, and;
wherein the means is configured to proportionally increase fluid flow resistance as vacuum levels increase.

* * * * *